(12) United States Patent
Ternes et al.

(10) Patent No.: US 10,166,398 B2
(45) Date of Patent: Jan. 1, 2019

(54) METHODS AND APPARATUS FOR MANAGING MULTIPLE CATHODE PACING

(71) Applicant: Cardiac Pacemakers, Inc., St. Paul, MN (US)

(72) Inventors: David J. Ternes, Roseville, MN (US); William J. Linder, Golden Valley, MN (US); Sunipa Saha, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 219 days.

(21) Appl. No.: 15/139,450

(22) Filed: Apr. 27, 2016

(65) Prior Publication Data

US 2016/0346552 A1 Dec. 1, 2016

Related U.S. Application Data

(60) Provisional application No. 62/169,293, filed on Jun. 1, 2015.

(51) Int. Cl.
| | |
|---|---|
| *A61N 1/00* | (2006.01) |
| *A61N 1/37* | (2006.01) |
| *A61N 1/05* | (2006.01) |
| *A61N 1/368* | (2006.01) |
| *A61B 5/053* | (2006.01) |
| *A61N 1/365* | (2006.01) |

(52) U.S. Cl.
CPC .......... *A61N 1/3712* (2013.01); *A61B 5/0538* (2013.01); *A61N 1/056* (2013.01); *A61N 1/3684* (2013.01); *A61N 1/3686* (2013.01); *A61N 1/36521* (2013.01)

(58) Field of Classification Search
CPC .... A61N 1/3712; A61N 1/0538; A61N 1/056; A61N 1/36521; A61N 1/3684; A61N 1/3686
See application file for complete search history.

(56) References Cited

U.S. PATENT DOCUMENTS

| | | |
|---|---|---|
| 7,319,900 B2 | 1/2008 | Kim et al. |
| 7,904,142 B2 | 3/2011 | Kim et al. |
| 7,945,327 B2 | 5/2011 | Gandhi et al. |
| 8,290,590 B2 | 10/2012 | Bohn et al. |

(Continued)

*Primary Examiner* — Lindsey G Wehrheim
(74) *Attorney, Agent, or Firm* — Schwegman Lundberg & Woessner, P.A.

(57) ABSTRACT

An apparatus comprises a stimulus circuit, a switch circuit, and a control circuit. The stimulus circuit is configured to provide electrical pulse stimulation to the plurality of electrodes. The switch circuit is configured to electrically couple different combinations of the electrodes to the stimulus circuit. The control circuit is to configure a stimulation vector that includes a first vector electrode and a plurality of other electrodes electrically coupled together to form a second combined vector electrode. The control circuit includes a capture detection sub-circuit configured to determine individual capture stimulation thresholds between the first vector electrode and each single electrode of the combined vector electrode. The control circuit is configured to determine a capture stimulation threshold of the stimulation vector using the determined individual capture thresholds.

20 Claims, 8 Drawing Sheets

(56) References Cited

U.S. PATENT DOCUMENTS

| | | |
|---|---|---|
| 8,565,879 B2 | 10/2013 | Brisben et al. |
| 8,886,313 B2 | 11/2014 | Siejko et al. |
| 9,636,504 B2 * | 5/2017 | Gilman .............. A61N 1/36542 |
| 2017/0021176 A1 * | 1/2017 | Badie ................... A61N 1/3686 |

* cited by examiner

“METHODS AND APPARATUS FOR MANAGING MULTIPLE CATHODE PACING

CLAIM OF PRIORITY

This application claims the benefit of priority under 35 U.S.C. § 119(e) of U.S. Provisional Patent Application Ser. No. 62/169,293, filed on Jun. 1, 2015, which is herein incorporated by reference in its entirety.

BACKGROUND

Implantable medical devices (IMDs) are implantable or partially implantable. Some examples include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of IMDs include implantable diagnostic devices, implantable drug delivery systems, or implantable devices with neural stimulation capability (e.g., vagus nerve stimulator, baroreflex stimulator, carotid sinus stimulator, deep brain stimulator, sacral nerve stimulator, etc.).

Operation of an IMB is typically optimized for particular patient by a caregiver, such as by programming different device operating parameters or settings for example. Manufacturers of such devices continue to improve and add functionality to the devices, which can make them complicated to program. The inventors have recognized a need for improved optimization of device-based therapy.

OVERVIEW

The present subject matter relates to providing multi-site electrical stimulation therapy. An example multi-site electrical stimulation therapy is multi-site pacing stimulation delivered to multiple sites within the same chamber of the heart.

An apparatus example of the present subject matter is for electrical coupling to a plurality of implantable electrodes. The apparatus example includes a stimulus circuit, a switch circuit, and a control circuit. The stimulus circuit provides electrical pulse stimulation to the plurality of electrodes. The switch circuit electrically couples different combinations of the electrodes to the stimulus circuit. The control circuit is to configure a stimulation vector that includes a first vector electrode and a plurality of other electrodes electrically coupled together to form a second combined vector electrode. The control circuit includes a capture detection subcircuit that determines individual capture stimulation thresholds between the first vector electrode and each single electrode of the combined vector electrode. The control circuit determines a capture stimulation threshold of the stimulation vector using the determined individual capture thresholds.

Using combined electrodes in a stimulation vector may add complexity to the programming of parameter values for electrical stimulation therapy. Device generated recommendations for values of parameters associated with the electrical stimulation may assist the clinician or physician to optimize the device for the needs of a specific patient.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

Figure 1:
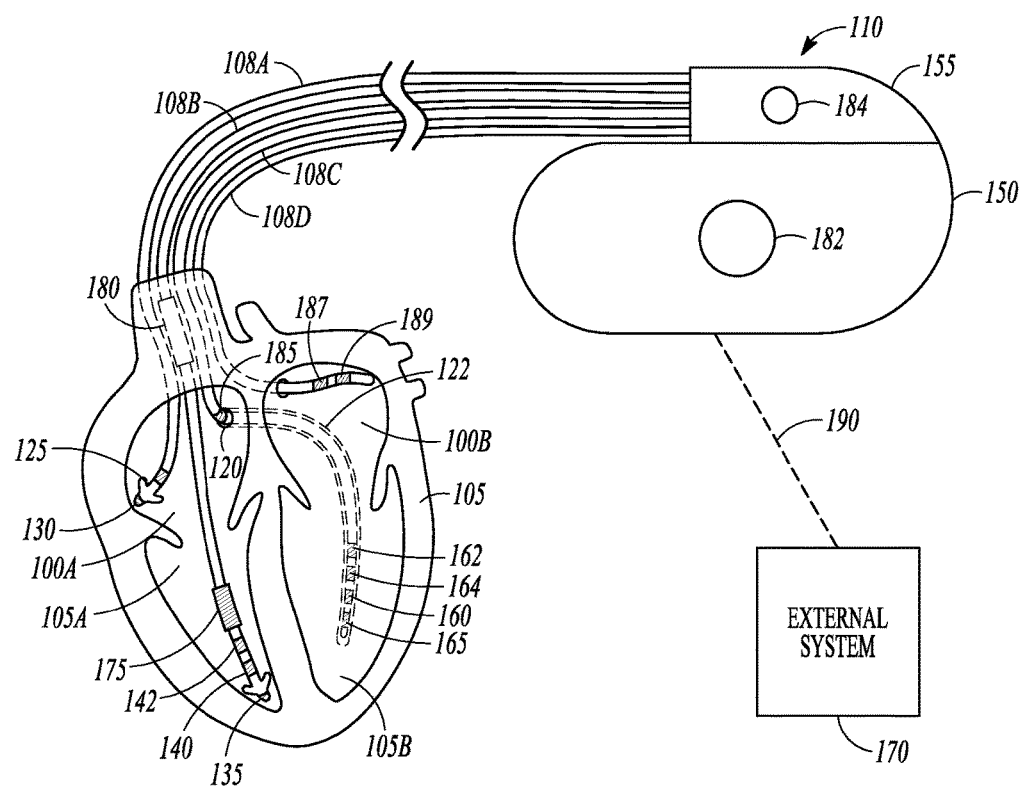
FIG. 1 is an illustration of an example of portions of a system that includes an implantable medical device.

An implantable medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions. FIG. 1 is an illustration of portions of a system that includes an IMB 110.

Examples of IMD 110 include, without limitation, a pacemaker, a defibrillator, a cardiac resynchronization therapy (CRT) device, or a combination of such devices. In other examples, the IMD is a neurostimulator such as among other things a vagus nerve stimulator, baroreflex stimulator, carotid sinus stimulator, deep brain stimulator, or sacral nerve stimulator. The system 100 also typically includes an IMB programmer or other external system 170 that communicates wireless signals 190 with the IMD 110, such as by using radio frequency (RF) or other telemetry signals.

The IMB 110 can be coupled by one or more leads 108A-D to heart 105. Cardiac leads 108A-D include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled cardiac signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. RV lead 108B can include one or more additional ring electrodes 142 to provide multi-site pacing to the RV. Lead 108B optionally also includes additional electrodes, such as electrodes 175 and 180, for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMB 110 can include a third cardiac lead 108C attached to the IMB 110 through the header 155. The third cardiac lead 108C includes electrodes 160, 162, 164, and 165 placed in a coronary vein 122 lying epicardially on the left ventricle (LV) 105B via the coronary vein. The number of electrodes shown in the Figure is only an example and other arrangements are possible. For instance, the third cardiac lead 108C may include less electrodes (e.g., one or two electrodes) or more electrodes (e.g., eight or more electrodes) than the example shown, and may include a ring electrode 185 positioned near the coronary sinus (CS) 120.

In addition to cardiac leads 108A, 108B, 108C, or in alternative to one or more of cardiac leads 108A, 108B, 108C, the IMD 110 can include a fourth cardiac lead 108D that includes electrodes 187 and 189 placed in a vessel lying epicardially on the left atrium (LA) 100B.

The IMB 110 can include a hermetically-sealed IMB housing or can 150, and the IMB 110 can include an electrode 182 formed on the IMB can 150. The IMB 100 may include an IMB header 155 for coupling to the cardiac leads, and the IMB header 155 may also include an electrode 184. Cardiac pacing therapy can be delivered in a unipolar mode using the electrode 182 or electrode 184 and one or more electrodes formed on a lead. Cardiac pacing therapy can be delivered in an extended bipolar pacing mode using only one electrode of a lead (e.g., only one electrode of LV lead 108C) and one electrode of a different lead (e.g., only one electrode of RV lead 108B). Cardiac pacing therapy can be delivered in a monopolar pacing mode using only one electrode of a lead without a second electrode.

Lead 108B can include a first defibrillation coil electrode 175 located proximal to tip and ring electrodes 135, 140 for placement in a right ventricle, and a second defibrillation coil electrode 180 located proximal to the first defibrillation coil electrode 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to the electrode 182 formed on the IMB can 150. This improves defibrillation by delivering current from the RV coil 175 more uniformly over the ventricular myocardium. In some examples, the therapy is delivered from the RV coil 175 only to the electrode 182 formed on the IMD can 150. In some examples, the coil electrodes 175, 180 are used in combination with other electrodes for sensing signals.

Note that the specific arrangement of leads and electrodes shown in the illustrated example of FIG. 1 is intended to be non-limiting. An IMD can be configured with a variety of electrode arrangements including transvenous, endocardial, and epicardial electrodes (e.g., an epicardial patch that may include dozens of electrodes), and/or subcutaneous, non-intrathoracic electrodes. An IMD 110 can be connectable to subcutaneous array or lead electrodes (e.g., non-intrathoracic electrodes or additional LV leads implantable along the LV wall, and leads implantable in one or both atria) that can be implanted in other areas of the body to help "steer" electrical currents produced by IMB 110. An IMB can be leadless (e.g., a leadless pacemaker). A leadless IMD may be placed in a heart chamber (e.g., RV or LV) and multiple electrodes of the leadless IMD may contact multiple tissue sites of the heart chamber. The present methods and systems will work in a variety of configurations and with a variety of electrodes.

For instance, a CRM device may be configured to provide multi-site pacing, in which electrical stimulation pulses are provided to multiple sites within the same heart chamber. This may be useful to improve coordination of a contraction of the heart chamber, especially contraction of the left ventricle. In the example shown in FIG. 1, electrically coupling multiple electrodes of the LV together into a combined electrode will provide electrical stimulation pulses to multiple sites in the LV. For instance, LV tip electrode 165 can be electrically coupled to LV ring electrode 162 to form a combined electrode. A stimulation vector can include electrode 182 as the anode and combined electrodes 165 and 162 as the cathode. Other combinations are possible. In another example, LV tip electrode 165 can be electrically coupled to LV ring electrode 164 to form the combined electrode. In another example, LV ring electrode 160 can be electrically coupled to LV ring electrode 162 to form the combined electrode. A stimulation vector can be formed using any of the combined electrodes and another electrode, such as an electrode located on the IMD, an electrode located in the RV, or an electrode positioned at one of the atria.

Some of the considerations in choosing electrodes for the combined electrode include the separation distance between electrodes, electrode tissue contact, electrode location, and presence of scar tissue at, near, or between electrode locations. In the example of FIG. 1, separation of LV electrodes 162 and 165 make these electrode good candidates for combining into one electrode. However, poor tissue contact at the location of one or more of the electrodes may dictate that a different combination of LV electrodes be used instead.

Configuring stimulation vectors that include a combined electrode can add complexity to the operation of the medical device. For instance, combining electrodes may lead to a stimulation vector that requires increased energy to capture the myocardial tissue. Capture of a cardiac tissue target refers to delivering electrical pacing stimulation energy to successfully induce cardiac depolarization and contraction. Capture can also refer to delivering electrical neurostimulation energy to induce the desired response in nerve tissue. Because IMDs are battery powered, it is desirable to optimize the stimulation energy to ensure therapy efficacy and yet avoid compromising battery life. This can be done by determining the minimum energy required to cause capture of the tissue target and then adding a safety margin to the minimum energy to ensure efficacy of the stimulation pulses.

The medical device itself can assist the clinician in setting parameters for proper electrical stimulation. An approach to determining a safety margin for device delivery of electrical pacing therapy can be found in Brisben et al., U.S. Pat. No. 8,565,879, "Method and Apparatus for Pacing Safety Margin," filed Mar. 25, 2011, which is incorporated herein by reference in its entirety.

Assistance by the medical device can be especially beneficial if the clinician would like information on configuring a large number or all of the possible stimulation vectors than can be formed using deployed electrodes. The example of FIG. 1 shows that a large number of stimulation vectors with a combined electrode are possible. The medical device may perform measurements and calculations to predict the stimulation capture threshold energy level of the stimulation vectors. In some examples, the medical device runs tests to determine the stimulation capture thresholds of the stimulation vectors.

Figure 2:
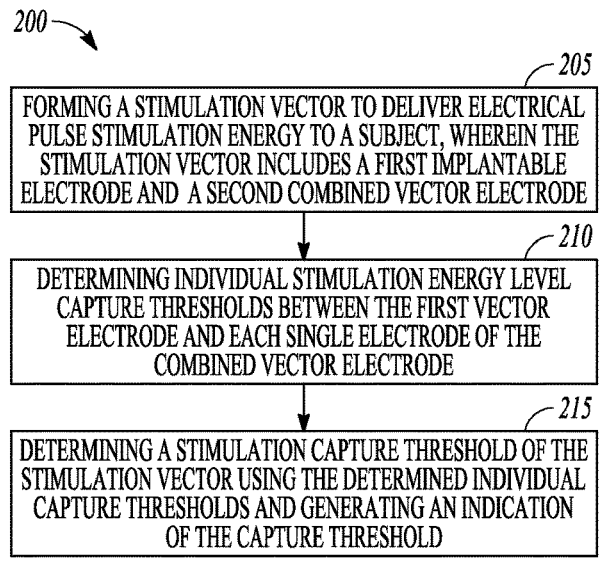
FIG. 2 shows a flow diagram of an example of a method of controlling operation of an implantable medical device.

FIG. 2 shows an example of a method 200 of controlling operation of an implantable medical device. At 205, a stimulation vector is formed to deliver electrical pulse stimulation energy to a patient or subject. The stimulation vector includes a first implantable electrode as the first vector electrode of the stimulation vector, and multiple other implantable electrodes electrically coupled together to form the second combined vector electrode of the stimulation vector. In certain variations, the electrodes are configured by shape and size to deliver the stimulation energy to a myocardial tissue target of the heart, and in some variations the electrodes are configured to deliver the stimulation energy to a nerve tissue target of the patient or subject, such as a phrenic nerve, a vagus nerve, or a tissue target of the spinal cord.

At 210, individual stimulation capture thresholds between the first vector electrode and each single electrode of the combined vector electrode are determined. These individual stimulation capture thresholds can be used at 215 to determine or predict the stimulation capture threshold of the stimulation vector. An indication of the capture threshold can then be generated. In some variations, the indication may be a value of the stimulation capture threshold communicated by the medical device to a separate device. In some variations, the indication is a value used by the medical device to set a minimum stimulation threshold. For instance, the medical device may add a safety margin to the determined stimulation capture threshold to set the minimum stimulation energy level.

Figure 3A:
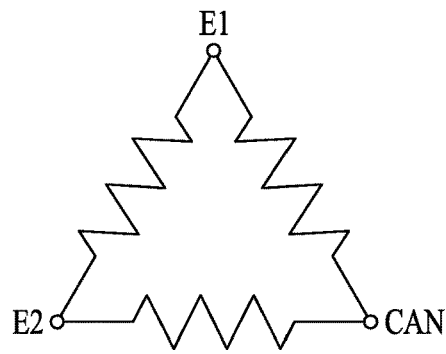
FIGS. 3A and 3B illustrate representations of a stimulation vector.

FIG. 3A illustrates a representation of an example of a stimulation vector. In an example intended to be non-limiting, electrode 1 (E1) may correspond to LV tip electrode 165 in FIG. 1, electrode 2 (E2) may correspond to LV ring electrode 162, and the electrode labeled "CAN" may correspond to electrode 182 formed on the IMB can. In certain variations, E1 and E2 are electrically coupled and function as the cathode of the stimulation vector and CAN electrode is the anode of the stimulation vector. To ensure capture at all electrically coupled electrodes using the combined stimulation vector, the current at electrode E1 should be greater than the capture threshold current at E1 and the current at E2 should be greater than the capture threshold current at E2.

Figure 4:
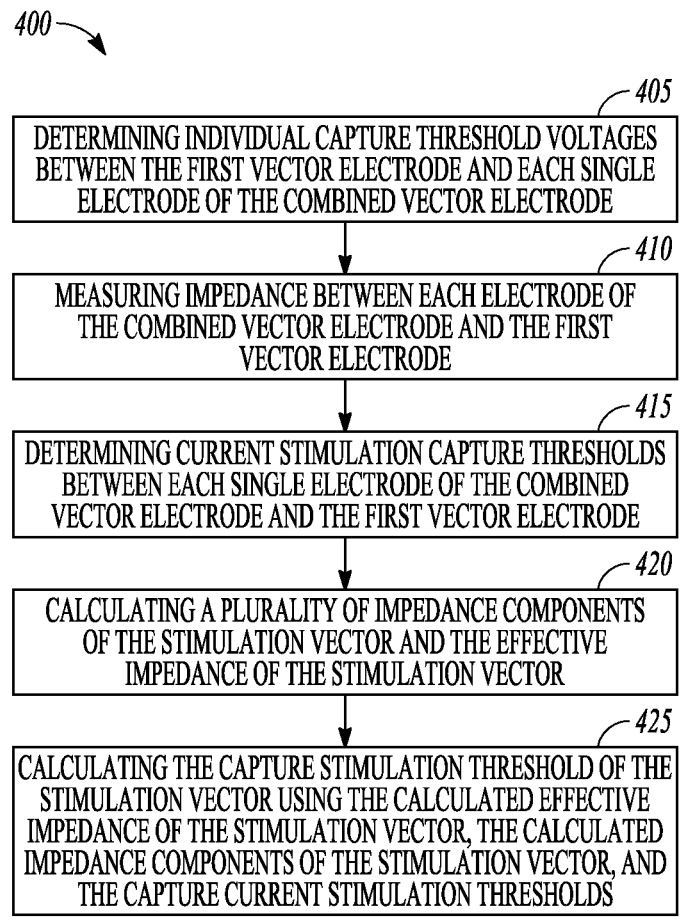
FIG. 4 shows a flow diagram of another example of a method of controlling a medical device

FIG. 4 shows a flow diagram of an example of a method 400 of controlling a medical device such as to determine the stimulation capture threshold for a stimulation vector. At 405, individual capture threshold voltages are determined between the first vector electrode and each single electrode of the combined vector electrode. In the example of FIG. 3A, a voltage stimulation capture threshold is determined for the stimulation vector including E1 to CAN while E2 is not electrically connected ($V_{E1toCAN}$), and a voltage stimulation capture threshold is determined for a stimulation vector including E2 to CAN while E1 is not electrically connected $V_{E2toCAN}$.

At 410, impedances between each electrode of the combined vector electrode and the first vector electrode are measured. As with the voltage thresholds, impedance is measured while none of the electrodes of the combined vector electrode are electrically connected together. For the stimulation vector shown in FIG. 3A, the impedance between electrodes E1 and CAN is measured while electrode E2 is not electrically coupled to electrode E1 ($R_{E1toCAN}$), and the impedance between electrodes E2 and CAN is measured while electrode E1 is not electrically coupled to electrode E2 ($R_{E2toCAN}$). The impedance between electrodes E1 and E2 can also be measured ($R_{E1toE2}$).

At 415, current stimulation capture thresholds are determined between each single electrode of the combined vector electrode and the first vector electrode using the measured impedances and the measured voltage stimulation capture thresholds. Ohms law can be used to calculate the current thresholds (e.g., by I=V/R). For instance, the current threshold from electrode E1 to CAN electrodes is calculated by $IE1=V_{E1toCAN}/(R_{E1toCAN})$ and the current threshold from electrode E2 to CAN electrodes is calculated by $IE2=V_{E2toCAN}/(R_{E2toCAN})$.

At 420, the impedance components of the stimulation vector are calculated. FIG. 3A shows the stimulation vector represented as a delta (Δ) arrangement of impedances. In some examples, the medical device calculates impedance components of an equivalent wye (Y) impedance arrangement.

Figure 3B:
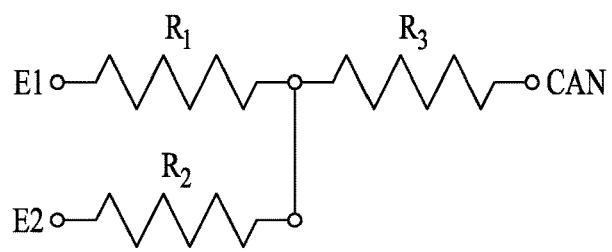

FIG. 3B illustrates a representation of an example of the equivalent wye arrangement of the stimulation vector of FIG. 3A. The impedance components R1, R2, and R3 are calculated using the measured impedances $R_{E1toCAN}$, $R_{E2toCAN}$, and $R_{E1toE2}$. For the transform of the delta arrangement to the wye arrangement, $R_{E1toE2}=R1+R2$, $R_{E1toCAN}=R1+R3$, and $R_{E2toCAN}=R2+R3$. Methods to obtain $R_{E1toCAN}$, $R_{E2toCAN}$, and $R_{E1toE2}$ were described previously herein.

From the impedance relationships, the following equations can be obtained:

$$R1=R_{E1toE2}-R2,$$

$$R2=R_{E2toCAN}-R3, \text{ and}$$

$$R3=R_{E1toCAN}-R1.$$

Solving for the component impedances yields:

$$R1=(R_{E1toCAN}-R_{E2toCAN}+R_{E1toE2})/2,$$

$$R2=(R_{E2toCAN}-R_{E1toCAN}+R_{E1toE2})/2, \text{ and}$$

$$R3=(R_{E1toCAN}-R_{E1toE2}+R_{E2toCAN})/2.$$

From the individual impedance components, the effective impedance of the stimulation vector can be determined as $$R_{EFF}=R1\|R2+R3=(1/((1/R1)+(1/R2)))+R3.$$

At 425, the capture stimulation threshold for the stimulation vector can be calculated using the calculated effective impedance of the stimulation vector, the calculated resistive components of the stimulation vector, and the capture current stimulation thresholds. For instance, the minimum voltage at E1 for capture is $$V_{E1}=I_{E1}*(R_{EFF}*(R1+R2))/R2,$$

and the minimum voltage at E2 for capture is $$V_{E2}=I_{E2}*R_{EFF}*(R1+R2))/R1.$$

The higher of $V_{E1}$ and $V_{E2}$ can be used as the device-determined capture stimulation threshold for capturing all sites of the combined stimulation electrode of the stimulation vector. In some examples, a safety margin is added to this voltage and used as the voltage value of the electrical pulse stimulation applied with the stimulation vector.

In some examples, the measured impedances $R_{E1toCAN}$, $R_{E2toCAN}$, and $R_{E1toE2}$ may be pre-qualified before the calculations performed or post qualified afterwards to determine if the measured impedance are within an acceptable range. This can avoid using impedance components in the calculation that are not valid (e.g., impedance components having a negative value). In some examples, the measurement of impedances $R_{E1toCAN}$, $R_{E2toCAN}$, and $R_{E1toE2}$ is constrained to occur within a specified duration of time. In some examples, the measurement of impedances $R_{E1toCAN}$, $R_{E2toCAN}$, and $R_{E1toE2}$ is constrained to occur in a specified relation to a detected R-wave of a cardiac cycle.

Although the method has been described using the arrangement of electrodes in FIG. 1, the description is intended to be non-limiting and the method 400 can be used with other electrode arrangements and with other stimulation vectors than the examples described. For instance, other electrodes can be used as the anode such as an electrode located in the RV, and there may be more than 4 electrodes arranged in the LV that can be candidates for use in a combined electrode. In certain variations, the first vector electrode is the cathode and the combined vector electrode is the anode of the stimulation vector. In certain variations, the combined electrode is formed by electrically coupling multiple electrodes arranged in the RV. In certain variations, the method 400 is performed using a medical device that is leadless. For instance, the medical device may be a leadless pacemaker with three or more electrodes formed on the device housing and positioned in a chamber of the heart. Multiple electrodes can be electrically connected to form the combined vector electrode.

Figure 5:
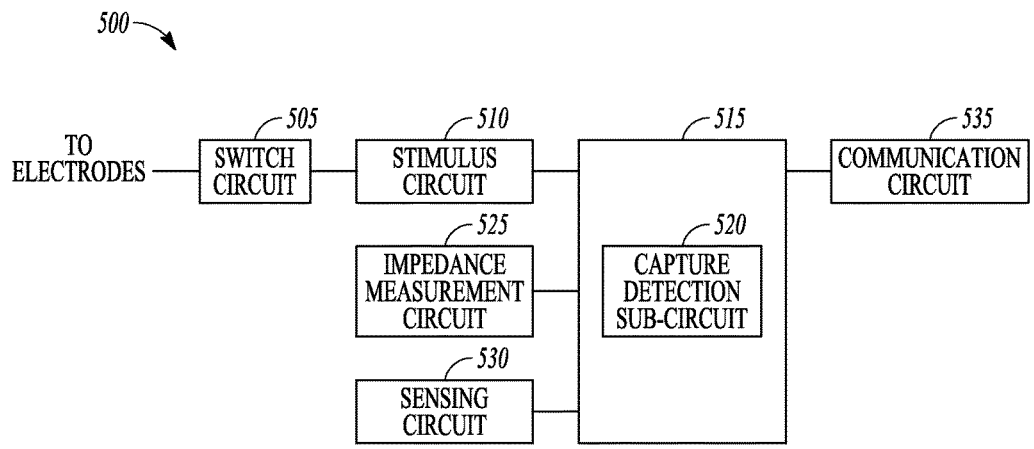
FIG. 5 shows a block diagram of portions of an example of a medical device.

FIG. 5 shows a block diagram of portions of a medical device. The device 500 can be coupled to multiple implantable electrodes, such as the electrode arrangement described in the example of FIG. 1. The device 500 includes a stimulus circuit 505, a switch circuit 510, and a control circuit 515. The stimulus circuit 505 provides electrical pulse stimulation to the plurality of electrodes. The switch circuit 510 electrically couples different combinations of the electrodes to the stimulus circuit 505. The control circuit 515 can include can include a microprocessor, a digital signal processor, application specific integrated circuit (ASIC), or other type of processor, interpreting or executing instructions included in software or firmware. The control circuit 515 can include sub-circuits to perform the functions described. These sub-circuits may include software, hardware, firmware or any combination thereof. Multiple functions can be performed in one or more of the sub-circuits as desired.

The control circuit 515 configures a stimulation vector that includes a first vector electrode and other electrodes electrically coupled together to form a second combined vector electrode. As explained previously in regard to FIG. 1, an example of a stimulation vector can include electrode 182 as the anode and combined electrodes 165 and 162 as the cathode when delivering stimulation energy.

Returning to FIG. 5, the control circuit 515 includes a capture detection sub-circuit 520 that determines individual capture stimulation thresholds between the first vector electrode and each single electrode of the combined vector electrode. The control circuit 515 then determines a capture stimulation threshold of the stimulation vector using the determined individual capture thresholds.

To determine individual capture stimulation thresholds, the control circuit 515 changes the stimulation vector to include the first vector electrode and a first single electrode of the combined vector electrode. The control circuit 515 initiates a determination by the capture detection sub-circuit 520 of a minimum stimulation energy level that induces capture of the tissue target as the capture stimulation threshold for the changed stimulation vector. When that minimum stimulation energy level is determined, the control circuit 515 changes the stimulation vector to include the first vector electrode and a second single electrode of the combined vector electrode, and repeats the determination by the capture detection sub-circuit 520 of the minimum stimulation energy level that induces capture. The control circuit 515 repeats the changing of the single electrode of the combined vector electrode and repeats the iterative stimulation energy delivery until a minimum stimulation energy level that induces capture is determined for a stimulation vector that includes the first vector electrode and each single electrode of the combined vector electrode.

The control circuit 515 may perform the method in the example of FIG. 4 to determine the capture stimulation threshold of the stimulation vector. The individual capture stimulation thresholds determined by the device 500 may be the individual capture voltage stimulation thresholds. The device 500 can include an impedance measurement circuit 525 that can be electrically coupled to the plurality of implantable electrodes. The impedance measurement circuit 525 measures the impedance between any two electrodes included in the stimulation vector. The impedance measurement circuit 525 may be electrically coupled to the electrodes through the switch circuit 505 to electrically couple different combinations of the electrodes to the impedance measurement circuit 525.

In some examples, the impedance measurement circuit 525 measures impedance between electrodes of the stimulation vector while none of the electrodes are electrically connected together to form the combined vector electrode. The impedance measurement circuit 525 also measures impedance of the combined vector electrode.

In some examples, the impedance measurement circuit 525 measures impedance using a non-stimulating excitation signal. For instance to measure impedance $R_{E1toCAN}$ in the example of FIG. 5, the impedance measurement circuit 525 applies a non-stimulating excitation current between electrodes E1 and CAN and measures the resulting voltage. The excitation current is non-stimulating because it has an amplitude lower than the minimum amplitude for pacing stimulation, i.e., it has a low enough amplitude that it does not trigger a heart depolarization. The measured voltage is divided by the known excitation current to obtain the impedance.

The individual voltage thresholds and individual impedance components are measured or calculated and used to determine the capture stimulation threshold of the stimulation vector.

In some examples, the device 500 provides pacing stimulation energy to a tissue target of the myocardium. The capture detection sub-circuit 520 delivers pacing stimulation energy to the tissue target using a first energy level. The capture detection sub-circuit 520 changes the stimulation energy level by at least one of: a) increasing the stimulation energy from the first energy level until detecting that the stimulation energy induces stable capture, or b) reducing the stimulation energy from the first energy level until detecting that the stimulation energy fails to induce capture of the tissue target. The capture detection sub-circuit 520 continues the changing of the stimulation energy level until confirming the stable capture or the failure to induce capture. The capture stimulation threshold energy is determined as the stimulation energy level that resulted in stable capture or the last energy stimulation level before failure to induce capture.

The device 500 includes a sensing circuit 530 that produces an electrical activation signal representative of activation of the tissue target. In some examples, the sensing circuit 530 is a cardiac signal sensing circuit that provides an electrical cardiac signal representative of cardiac activity. When decreasing the stimulation energy, failure to induce capture can be detected by the different morphology of the signal corresponding to capture as compared to the morphology of the non-capture signals. For instance, a signal corresponding to non-capture may show a delayed response as compared to the morphology of the capture signals. Similarly, for the test where energy is increased, capture is evident in the cardiac signal by the different morphology as compared to the morphology of the non-capture traces. An approach for an automatic capture threshold test can be found in Kim et al., "Capture Detection with Cross Chamber Backup Pacing," U.S. Pat. No. 7,319,900, filed Dec. 11, 2003, which is incorporated herein by reference in its entirety. The individual voltage thresholds and individual impedance components are measured or calculated and can be used by the control circuit 515 to determine the capture stimulation threshold of the stimulation vector and generate a recommended minimum pacing stimulation energy for the stimulation vector.

In some examples, the capture detection sub-circuit 520 directly measures the current stimulation capture thresholds during the capture detection test. In this case, the determining of the voltage current stimulation capture thresholds at 405 in the method of FIG. 4 does not need to be performed. The measuring of the current stimulation capture thresholds and the measuring of the impedances can be performed in any order.

In some examples, the control circuit 515 initiates testing of a second stimulation vector and generates a recommended minimum pacing stimulation energy for the second stimulation vector. The control circuit 515 may be programmed with electrode combinations to include in the tests and the control circuit 515 continues testing to determine a recommended minimum pacing stimulation energy for the programmed stimulation vectors. In some examples, the medical device includes a communication circuit 535 configured to communicate information with a second separate device. The control circuit 515 may receive the electrode combinations to include in the capture tests from the separate device.

According to some examples, the electrodes of the combined vector electrode are not electrically disconnected when determining a capture threshold of the stimulation vector, and the combined vector remains electrically connected during the testing. The capture detection sub-circuit 520 iteratively delivers stimulation energy to a tissue target of the subject while changing the stimulation energy level, and determines a minimum stimulation energy level that induces capture of the tissue target by the combined vector electrode.

Figure 6:
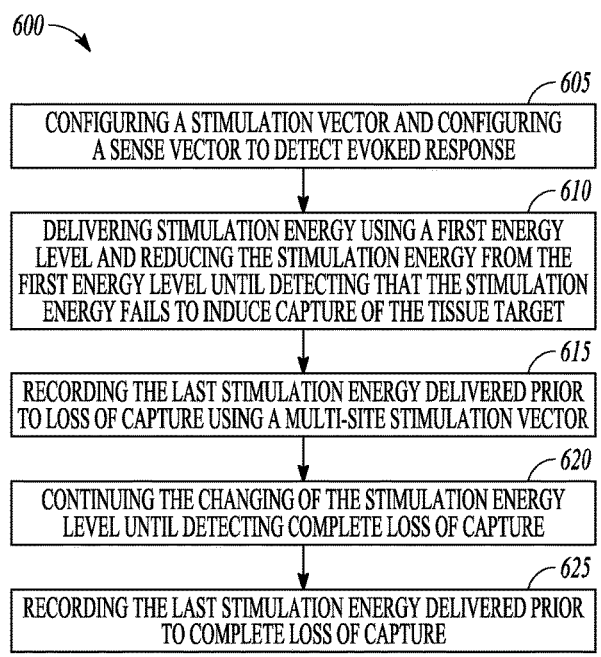
FIG. 6 shows a flow diagram of another example of a method of controlling a medical device.

FIG. 6 shows a flow diagram of another example of a method 600 of controlling a medical device to determine the stimulation capture threshold for a stimulation vector. At 605, a stimulation vector that includes a first vector electrode and a combined vector electrode is configured by the control circuit 515 of FIG. 5 as described previously herein. A sense vector may be configured by the control circuit 515 to sense an activation signal used to detect the evoked response resulting from the stimulation energy delivered using the stimulation vector. In some examples, the sense vector may include one or more of the electrodes used in the combined electrode of the stimulation vector. The electrodes of the sense vector can be electrically connected to sense amplifiers of the sensing circuit 530 of FIG. 5 by the switch circuit 505. In some examples, the control circuit 515 configures a sense vector using two or more electrodes separate from the stimulation vector for detecting induced capture or loss of capture. For instance, the control circuit 515 may configure a stimulation vector to include electrodes 162, 165 and 182 in the arrangement of FIG. 1, and configure a sense vector to include electrodes 164 and 184.

At 610, the capture detection sub-circuit 520 uses the stimulation vector to iteratively deliver stimulation energy to the tissue target while changing the stimulation energy level. The stimulation energy level may be iteratively reduced until detecting that the stimulation energy fails to induce capture of the multi-site tissue target. The failure to induce capture may be determined using the signal sensed by the sense vector. For instance, the sensed signal may include a representation of depolarization sensed at or near the target tissue site. The failure to induce capture can be detected by a change in morphology of the signal sensed with the sensing vector.

According to some examples, the capture detection sub-circuit 520 iteratively reduces the stimulation energy from a first energy level until detecting that a first single electrode of the combined vector electrode fails to induce capture.

Figure 7A:
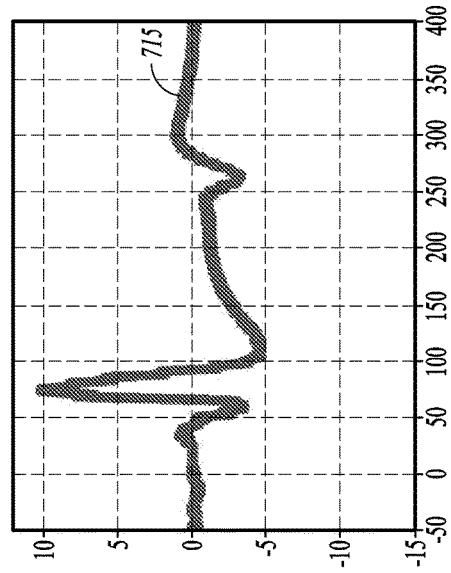
FIGS. 7A-7D show waveforms of an example of detecting when multi-site stimulation fails to induce capture of a tissue target.
Figure 7B:
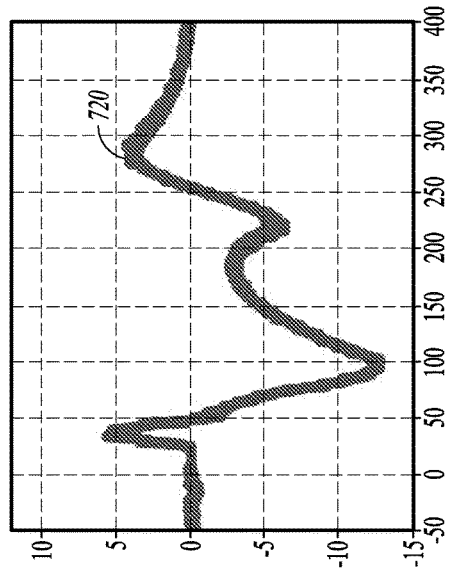
Figure 7C:
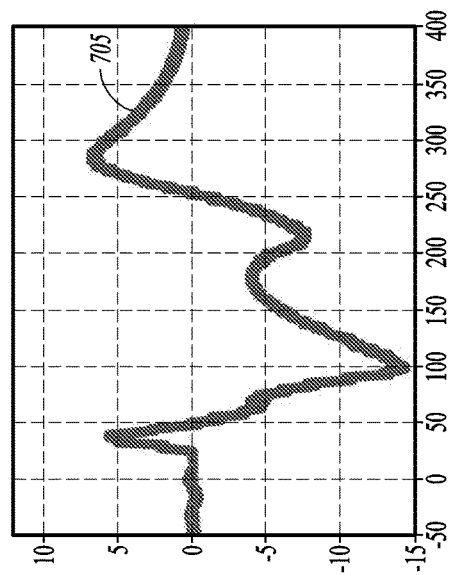
Figure 7D:
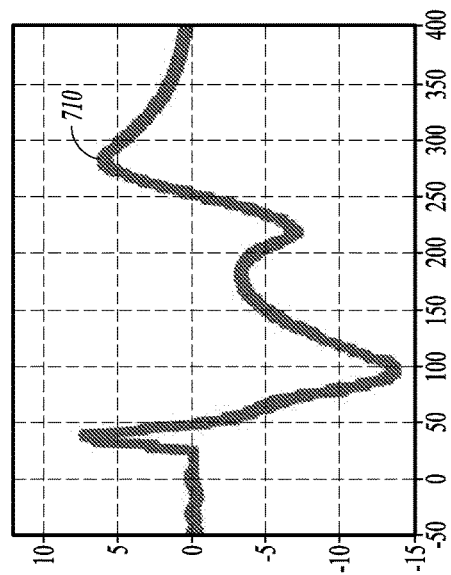

FIGS. 7A-7D shows waveforms of an example of detecting when stimulation energy fails to induce capture at all sites of the multi-site target. In the example, the stimulation vector is configured with a CAN electrode as the first vector electrode (e.g., electrode 182 in FIG. 1) and with two LV electrodes LV1 and LV2 (e.g., electrodes 165 and 160 in FIG. 1, respectively) as a combined vector electrode. The two waveforms 705 and 710 in FIGS. 7A and 7C are sensed using a sense vector that includes electrode LV1 and the CAN electrode, and the two waveforms 715 and 720 in FIGS. 7B and 7D are sensed using a sense vector that includes electrode LV2 and the CAN electrode.

The two waveforms 710 and 720 in FIGS. 7C and 7D show signals sensed after stimulation energy of 1.0 volts (1.0V) is delivered using the stimulation vector. The two waveforms 705 and 715 in FIGS. 7A and 7B show signals sensed after stimulation energy of 0.5V is delivered using the stimulation vector. The morphology of the signals sensed using sense vector LV1 to CAN stays the same while the morphology of the signals sensed using sense vector LV2 to CAN changes between the two stimulation energy levels. The change in morphology shows that the 0.5V stimulation at electrode LV2 fails to induce capture and localized depolarization at LV2. The morphology of the waveform at LV2 at 0.5V stimulation may be the depolarization wavefront from the capture induced at LV1 arriving at the LV2 electrode. The capture detection sub-circuit 520 of FIG. 5 may generate an indication to identify the first single electrode of the combined vector electrode (e.g., LV2 in the examples of FIGS. 7A-7D) that fails to induce capture first as the stimulation energy is reduced.

Figure 8A:
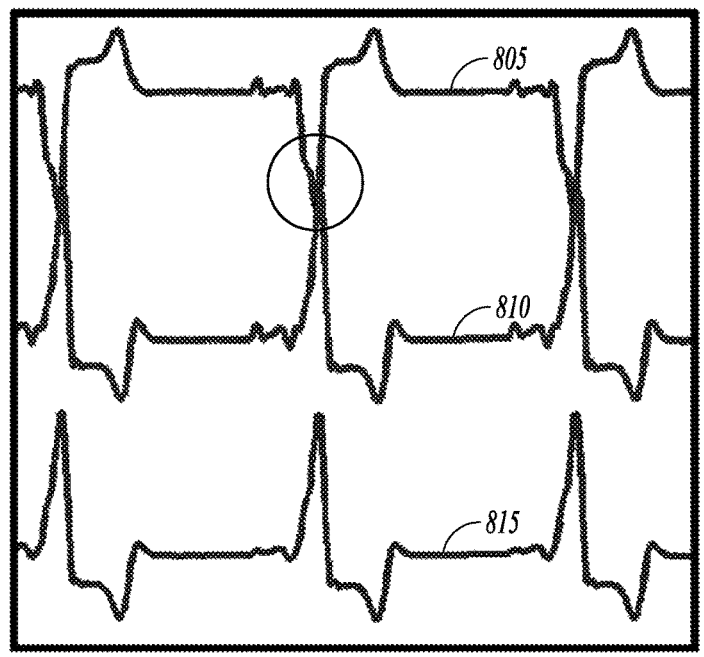
FIGS. 8A and 8B show waveforms of another example of detecting when multi-site stimulation fails to induce capture.
Figure 8B:
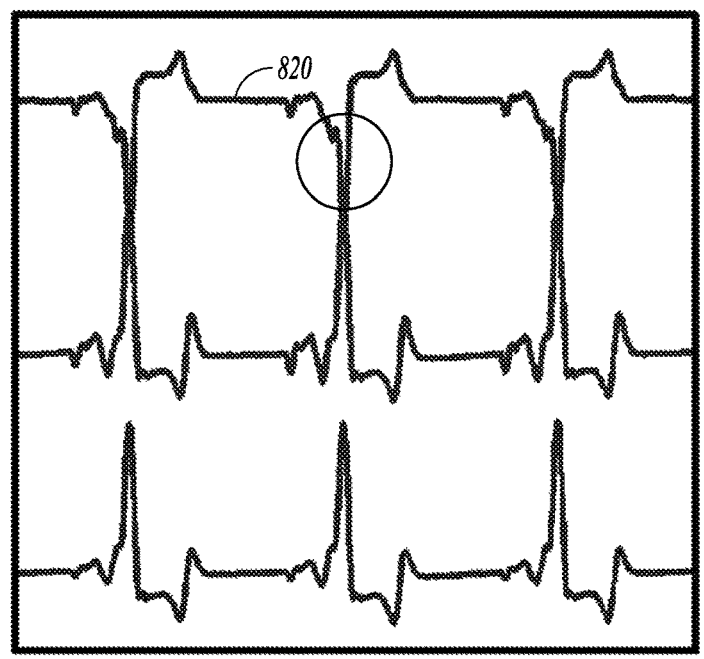

FIGS. 8A and 8B show waveforms of another example of detecting when stimulation energy fails to induce capture of at all sites of the multi-site target. The waveforms in FIG. 8A show cardiac depolarization resulting from stimulation delivered using a stimulation vector that includes CAN electrode (e.g., electrode 182 in FIG. 1) as the anode and 2 LV electrodes as the combined vector electrode (e.g., electrodes 165 and 162 in FIG. 1) as the cathode. The top waveforms 805 and 810 are electrograms sensed using device-based sensing channels. The bottom waveform 815 is a sensed electrocardiograph (ECG) signal.

The waveforms in FIG. 8B show cardiac depolarization resulting from stimulation delivered using a stimulation vector that includes the CAN electrode and 1 LV electrode (e.g., electrode 165) as the cathode. The circled portion of waveform 805 and the circled portion of waveform 820 show the change in signal morphology between the multi-site capture with the combined cathode and capture with the single cathode. The example shows that the change in morphology may be too subtle for a clinician detect visually or manually.

Device-based detection can detect subtle changes in morphology. For instance, the control circuit 515 of the device 500 of FIG. 5 may determine a correlation value between electrogram signals sensed between successive steps of a capture threshold test. An example of a correlation value is feature correlation coefficient (FCC). The FCC can provide an indication of a degree of similarity between the shapes of the electrogram signals. When the FCC value changes to a value greater than a specified FCC threshold value, the morphology between the successive electrogram signals may have changed sufficiently to indicate a shift from multi-site capture to single-site capture. An approach to calculating a correlation value can be found in Kim et al., U.S. Pat. No. 7,904,142 filed May 16, 2007, which is incorporated herein by reference in its entirety. Device-based detection can be easier than visual or manual detection by a clinician and device-based detection can be performed in real time as the stimulation threshold test is performed.

Returning to FIG. 6 at 615, the last stimulation energy delivered prior to detecting loss of capture using the multi-site stimulation vector is recorded (e.g., stored in memory) by the medical device. If the capture detection sub-circuit 520 generates an indication that identifies the first electrode that fails to induce the stimulation, the medical device may record both the electrode that failed to induce capture and the last stimulation energy delivered prior to loss of capture.

At 620, the capture detection sub-circuit 520 continues the changing of the stimulation energy level until detecting complete loss capture. Complete loss of capture means that capture of the target tissue does not occur with any of the electrodes of the combined electrode.

Figure 9:
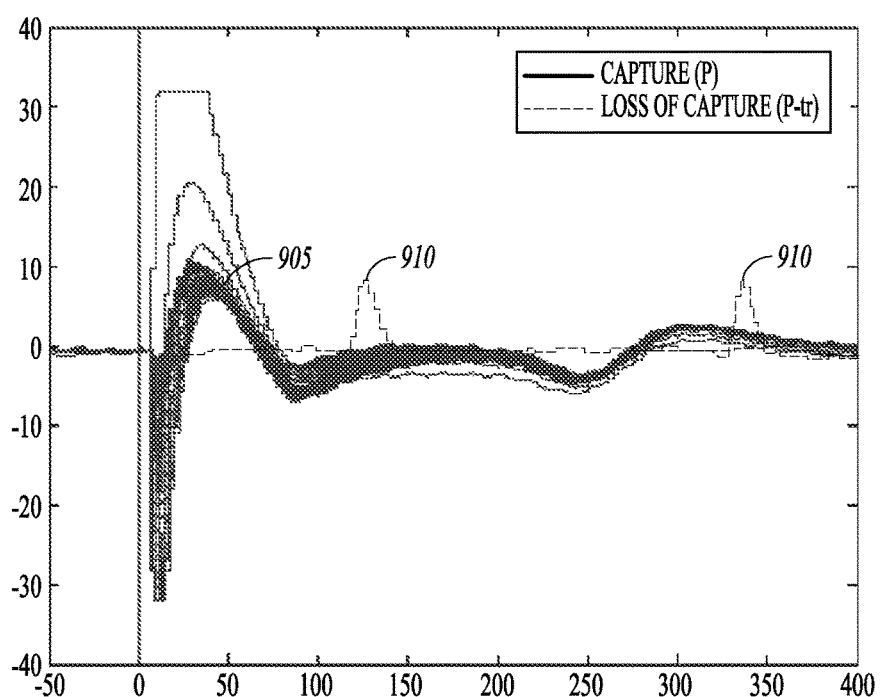
FIG. 9 shows waveforms of an example of detecting when single-site stimulation fails to induce capture.

FIG. 9 shows waveforms of an example of detecting when single-site stimulation energy fails to induce capture. In the example, the stimulation vector includes an LV electrode as the cathode and an RV electrode (e.g., ring electrode 140 in FIG. 1) as the anode. The sensing vector includes a CAN electrode and the LV electrode. The example shows a change in the morphology of the sensed cardiac activation signal between capture 905 and loss of capture 910. Loss of capture is evident in the delayed response as compared to the morphology of the capture signals. In some examples, the complete loss of capture can be detected from such a change in morphology of the sensed signals. In some examples, the complete loss of capture can be determined when cardiac contraction is not detected within a specified period of time of delivering the stimulation energy.

Returning to FIG. 6 at 625, the last stimulation energy delivered prior to complete loss of capture is recorded by the medical device. In some examples, the control circuit 515 determines a minimum stimulation energy level for the electrical therapy using the threshold determined for complete loss of capture. For instance, the control circuit 515 may add a safety margin to the last stimulation energy delivered prior to complete loss of capture as the minimum stimulation energy level. In some examples, the control circuit 515 determines the minimum stimulation energy level for the electrical therapy using the recorded last stimulation energy delivered prior to loss of capture by the multi-site stimulation vector. For instance, the control circuit 515 may add a safety margin to the stimulation energy recorded at 615 of the method of FIG. 6 to determine the minimum stimulation energy level for the electrical therapy.

The example of FIG. 6 is described in terms of a stimulation threshold test that reduces the stimulation energy until capture of the tissue target is lost. Alternatively the stimulation threshold test may begin with a stimulation energy level unlikely to cause capture and the test then increases the energy level until capture of the tissue target is detected. The stimulation energy level may be raised until capture is detected by one electrode of the combined electrode. One or both of the stimulation energy level and the electrode may be recorded at this point of the stimulation test. The stimulation energy level may then be increased until multi-site capture is detected due to capture by both electrodes of the combined electrode. The minimum stimulation energy level for the electrical therapy can be determined using the recorded energy levels. Additionally, while the threshold test has been described on terms of cardiac capture the stimulation threshold test could be applied to other types of tissue targets such as tissue target associated with the nervous system of a patient.

The stimulation threshold tests described herein can be performed while the patient is ambulatory and is not restricted to being performed in a clinical setting. In some examples, if the stimulation threshold for multi-site pacing is too high, the control circuit 515 of FIG. 5 may revert to single electrode stimulation from multi-site. The control circuit 515 may generate an indication (e.g., store a flag in memory) of the device-based decision to revert to single site stimulation.

When the control circuit 515 configures a new stimulation vector it may impact the longevity of the battery. The impedance seen by the stimulation circuit may change as a result of the new stimulation vector and the new vector may require higher stimulation energy because of either an increase in amplitude or pulse width. In some examples, the control circuit 515 calculates an effective impedance of the stimulation vector. The control circuit 515 may initiate measurements of the impedance between any two electrodes included in the stimulation vector by the impedance measurement circuit 525. The control circuit 515 then calculates the effective impedance of the stimulation vector using the measured impedances, such as by the method to calculate $R_{EFF}$ described previously herein in regard to FIG. 3. The control circuit 515 also determines the capture stimulation energy level threshold of the stimulation vector by any of the methods described previously herein.

In some examples, the control circuit 515 may then calculate the longevity of the battery of the implantable medical device using the determined effective impedance and the determined capture stimulation threshold of the stimulation vector. For instance, the control circuit 515 may calculate the amount of charge delivered per pulse by calculating the amount of current delivered per pulse and multiplying by the pulse width. The amount of current is the minimum stimulation voltage amplitude V (e.g., determined from the capture stimulation threshold) divided by the determined effective impedance $R_{EFF}$, and the amount of charge delivered per pulse is $(V/R_{EFF})*(Pulse Width)$.

In some examples, the control circuit 515 recalculates the battery longevity whenever a parameter related to the delivery of the electrical stimulation changes. The control circuit 515 may recalculate the longevity of the battery of the ambulatory medical device using the changed parameter value, the determined capture stimulation threshold, and the determined effective impedance. Some examples of the parameters include the stimulation vector, the stimulation amplitude, and the stimulation pulse width. Because the stimulation vector changes when stimulation mode changes between single-site and multi-site pacing, the control circuit 515 may recalculate battery longevity when the stimulation mode changes. In some examples, the value of the parameter is received via the communication circuit 535 and control circuit 515 recalculates the battery longevity when receiving the parameter value.

In certain examples, a user selects a stimulation vector using an external device and the external device programs the stimulation vector. Battery longevity is calculated for the programmed stimulation vector. In certain variations, battery longevity is calculated for all available stimulation vectors and the battery longevity for each available vector is presented to the user.

In certain examples, the battery longevity calculations could be performed using a combination of the external device and the implantable medical device. For instance, the implantable device may communicate impedance information to an external device (e.g., a medical device programmer) and the external device calculates the battery longevity of the implantable device using the parameter values of the stimulation energy delivery.

Figure 10:
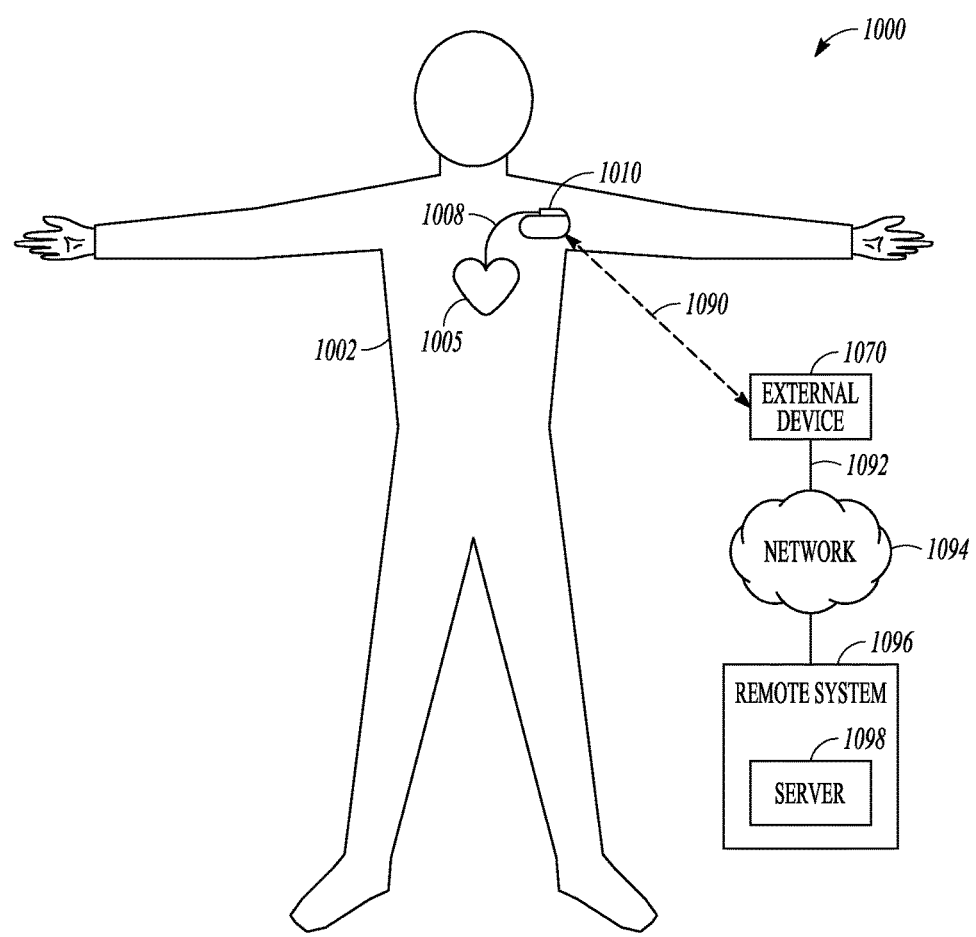
FIG. 10 is an illustration of portions of an example of a system that uses a deployed implantable medical device to provide a therapy to a patient.

FIG. 10 is an illustration of portions of an example of a system 1000 that uses a deployed IMD 1010 to provide a therapy to a patient 1002. The system 1000 typically includes an external device 1070 that communicates with a remote system 1096 via a network 1094. The network 1094 can be a communication network such as a cellular phone network or a computer network (e.g., the internet). In some examples, the external device 1070 includes a repeater and communicated via the network using a link 1092 that may be wired or wireless. In some examples, the remote system 1096 provides patient management functions and may include one or more servers 1098 to perform the functions. In some examples, the remote system 1096 provides electrode activation information for use with the methods of multi-site pacing described previously. For instance, the remote system 1096 may enable multi-site or single-site stimulation, or may indicate a stimulation vector with a combined vector electrode that is to be configured by the control circuit of the IMD 1010. The remote system 1096 may also communicate other stimulation parameters to the IMD 1010.

The devices and methods described herein allow for multi-site stimulation to be delivered to the subject with the minimum stimulation energy required for effective therapy. The device may provide additional information related to the multi-site pacing to assist the clinician or caregiver in managing the device-based therapy.

Additional Notes and Examples

Example 1 can include subject matter (such as an apparatus) comprising a stimulus circuit configured to provide electrical pulse stimulation to the plurality of electrodes; a switch circuit configured to electrically couple different combinations of the electrodes to the stimulus circuit; and a control circuit to configure a stimulation vector that includes a first vector electrode and a plurality of other electrodes electrically coupled together to form a second combined vector electrode. The control circuit includes a capture detection sub-circuit configured to determine individual capture stimulation energy level thresholds between the first vector electrode and each single electrode of the combined vector electrode; and wherein the control circuit is configured to determine a capture stimulation energy level threshold of the stimulation vector using the determined individual capture thresholds.

In Example 2, the subject matter of Example 1 optionally includes an impedance measurement circuit electrically coupled to the plurality of implantable electrodes and configured to measure the impedance between any two electrodes included in the stimulation vector. The capture detection sub-circuit is optionally configured to determine individual current stimulation capture thresholds between the first vector electrode and each single electrode of the combined vector electrode, and the control circuit is optionally configured to calculate an effective impedance of the stimulation vector using impedances measured by the impedance measurement circuit, and calculate the capture stimulation threshold using the calculated effective impedance of the stimulation vector and the individual current stimulation capture thresholds.

In Example 3, the subject matter of Example 2 optionally includes an impedance measurement circuit configured to measure impedances between each electrode of the combined vector electrode and the first vector electrode, wherein an impedance is measured while none of the plurality of electrodes are electrically connected together to form the combined vector electrode. The capture detection sub-circuit is optionally configured to measure individual capture voltage stimulation thresholds between the first vector electrode and each electrode of the combined vector electrode, and the control circuit is optionally configured to calculate the capture current stimulation thresholds using the measured impedances and capture voltage stimulation thresholds.

In Example 4, the subject matter of one or both of Examples 2 and 3 optionally includes a control circuit configured to calculate a plurality of impedance components of the stimulation vector and calculate the capture stimulation threshold of the stimulation vector using the calculated effective impedance of the stimulation vector, the calculated impedance components of the stimulation vector, and the capture current stimulation thresholds.

In Example 5, the subject matter of one or any combination of Examples 1-4 optionally includes a stimulus circuit configured to deliver electrical pacing stimulation to the implantable electrodes, and wherein the control circuit is configured to generate a recommended minimum pacing stimulation energy for the stimulation vector using the determined capture stimulation threshold of the stimulation vector.

In Example 6, the subject matter of one or any combination of Examples 1-5 optionally includes a first vector electrode that is an anode of the stimulation vector and the combined vector electrode is a cathode of the stimulation vector.

In Example 7, the subject matter of one or any combination of Examples 1-6 optionally includes a control circuit configured to change the stimulation vector to include the first vector electrode and a first single electrode of the combined vector electrode; initiate a determination of a minimum stimulation energy level that induces capture of the tissue target as the capture stimulation threshold for the changed stimulation vector; change the stimulation vector to include the first vector electrode and a second single electrode of the combined vector electrode and repeat the determination of the minimum stimulation energy level that induces capture; and repeat the changing of the single electrode of the combined vector electrode and repeat the iterative stimulation energy delivery until a minimum stimulation energy level that induces capture is determined for a stimulation vector that includes the first vector electrode and each single electrode of the combined vector electrode.

In Example 8 the subject matter of Example 7 optionally includes a capture detection sub-circuit configured to deliver pacing stimulation energy to the tissue target using a first energy level; change the stimulation energy level by at least one of: a) increasing the stimulation energy from the first energy level until detecting that the stimulation energy induces stable capture, or b) reducing the stimulation energy from the first energy level until detecting that the stimulation energy fails to induce capture of the tissue target; continue the changing of the stimulation energy level until confirming the stable capture or the failure to induce capture; and determine the capture stimulation threshold energy as the stimulation energy level that resulted in stable capture or the last energy stimulation level before failure to induce capture.

In Example 9, the subject matter of one or any combination of Examples 1-8 optionally includes an impedance measurement circuit electrically coupled to the plurality of implantable electrodes and configured to measure the impedance between any two electrodes included in the stimulation vector. The control circuit is optionally configured to calculate an effective impedance of the stimulation vector using impedances measured by the impedance measurement circuit, and calculate longevity of a battery of the implantable medical device using the determined effective impedance and the determined capture stimulation threshold of the stimulation vector.

In Example 10, the subject matter of Example 9 optionally includes a communication circuit configured to communicate information with a second separate device, including to receive a value for a parameter of the electrical pulse stimulation energy, wherein the control circuit is configured to calculate the longevity of the battery of the ambulatory medical device using the received parameter value, the determined capture stimulation threshold, and the determined effective impedance.

Example 11 can include subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-10 to include such subject matter, comprising configuring a stimulation vector to deliver electrical pulse stimulation energy to a subject, wherein the stimulation vector includes a first implantable electrode as a first vector electrode and a plurality of other implantable electrodes electrically coupled together to form a second combined vector electrode; determining individual stimulation energy level capture thresholds between the first vector electrode and each single electrode of the combined vector electrode; and determining a stimulation capture threshold of the stimulation vector using the determined individual capture thresholds and generating an indication of the capture threshold.

In Example 12, the subject matter of Example 11 optionally includes calculating an effective impedance of the stimulation vector, wherein determining individual stimulation energy level capture thresholds includes determining current stimulation capture thresholds between each single electrode of the combined vector electrode and the first vector electrode, and wherein determining the stimulation capture threshold of the stimulation vector includes calculating the stimulation capture threshold using the calculated effective impedance of the stimulation vector and the current stimulation capture thresholds.

In Example 13, the subject matter of Example 12 optionally includes measuring capture voltage stimulation thresholds between the first vector electrode and each electrode of the combined vector electrode; measuring impedances between each electrode of the combined vector electrode and the first vector electrode, wherein an impedance is measured while none of the plurality of electrodes are electrically connected together to form the combined vector electrode; and calculating the capture current stimulation thresholds using the measured impedances and capture voltage stimulation thresholds.

In Example 14, the subject matter of one or both of Examples 12 and 13 optionally includes calculating a plurality of resistive components of the stimulation vector and wherein determining the capture stimulation threshold of the stimulation vector includes calculating the capture stimulation threshold using the calculated effective impedance of the stimulation vector, the calculated resistive components of the stimulation vector, and the capture current stimulation thresholds.

In Example 15, the subject matter of one or any combination of Examples 12-14 optionally includes changing the stimulation vector to include the first vector electrode and a first single electrode of the combined vector electrode; iteratively delivering stimulation energy to a tissue target of the subject while changing a stimulation energy level; determining a minimum stimulation energy level that induces capture of the tissue target as the capture stimulation threshold; changing the stimulation vector to include the first vector electrode and a second single electrode of the combined vector electrode and repeating the iterative stimulation energy delivery and the determining of the minimum stimulation energy level that induces capture; and repeating the changing of the single electrode of the combined vector electrode and repeating the iterative stimulation energy delivery until minimum stimulation energy levels that induce capture are determined for stimulation vectors that includes the first vector electrode and each single electrode of the combined vector electrode.

In Example 16, the subject matter of one or any combination of Examples 11-15 optionally includes electrically coupling the plurality of implantable electrodes to form a combined cathode of the stimulation vector and wherein the first vector electrode is an anode of the stimulation vector.

Example 17 can include subject matter (such as an apparatus) or can optionally be combined with the subject matter of one or any combination of Examples 1-16 to include such subject matter, comprising: a stimulus circuit configured to provide electrical pulse stimulation to the plurality of electrodes; a switch circuit configured to electrically couple different combinations of the electrodes to the stimulus circuit; and a control circuit to configure a stimulation vector that includes a first vector electrode and a plurality of other electrodes electrically coupled together to form a second combined vector electrode, wherein the control circuit includes a capture detection sub-circuit configured to iteratively deliver stimulation energy to a tissue target of the subject while changing a stimulation energy level; and determine a minimum stimulation energy level that induces capture of the tissue target by the combined vector electrode, and wherein the control circuit is configured to calculate a capture stimulation energy level threshold for the stimulation vector using the minimum stimulation energy level.

In Example 18, the subject matter of Example 17 can optionally include a capture detection sub-circuit configured to determine a minimum stimulation energy level that induces capture of the tissue target by only one electrode of the combined vector electrode, and wherein the control circuit is configured to calculate the capture stimulation threshold for the stimulation vector using the minimum stimulation energy level that induces capture of the tissue target by only one electrode of the combined vector electrode.

In Example 19, the subject matter of one or both of Examples 17 and 18 optionally includes a sensing circuit configured to produce an electrical activation signal representative of activation of the tissue target, wherein the capture detection sub-circuit is configured to detect at least one of induced capture of the tissue target or failure to induce capture of the tissue target by detecting a change in morphology of the electrical activation signal.

In Example 20, the subject matter of Example 19 optionally includes a capture detection sub-circuit configured to iteratively reduce the stimulation energy from a first energy level until detecting that a first single electrode of the combined vector electrode fails to induce capture and to generate an indication to identify the first single electrode of the combined vector electrode.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus for electrical coupling to a plurality of implantable electrodes, the apparatus comprising:
   a stimulus circuit configured to deliver electrical pacing stimulation to the plurality of implantable electrodes;
   a switch circuit configured to electrically couple different combinations of the plurality of implantable electrodes to the stimulus circuit; and
   a control circuit to configure a stimulation vector that includes a first electrode of the plurality of implantable electrodes as a first vector electrode and multiple other electrodes of the plurality of implantable electrodes electrically coupled together to form a second combined vector electrode, wherein the control circuit includes a capture detection sub-circuit configured to determine individual capture stimulation energy level thresholds between the first vector electrode and each single electrode of the combined vector electrode; and wherein the control circuit is configured to determine a capture stimulation energy level threshold of the stimulation vector using the determined individual capture thresholds.

2. The apparatus of claim 1, including:
   an impedance measurement circuit electrically coupled to the plurality of implantable electrodes and configured to measure the impedance between any two electrodes of the plurality of implantable electrodes included in the stimulation vector,
   wherein the capture detection sub-circuit is configured to determine individual current stimulation capture thresholds between the first vector electrode and each single electrode of the combined vector electrode, and
   wherein the control circuit is configured to calculate an effective impedance of the stimulation vector using impedances measured by the impedance measurement circuit, and calculate the capture stimulation threshold using the calculated effective impedance of the stimulation vector and the individual current stimulation capture thresholds.

3. The apparatus of claim 2,
   wherein the impedance measurement circuit is configured to measure impedances between each electrode of the combined vector electrode and the first vector electrode, wherein an impedance is measured while none of the plurality of electrodes are electrically connected together to form the combined vector electrode,
   wherein the capture detection sub-circuit is configured to measure individual capture voltage stimulation thresholds between the first vector electrode and each electrode of the combined vector electrode, and
   wherein the control circuit is configured to calculate the capture current stimulation thresholds using the measured impedances and capture voltage stimulation thresholds.

4. The apparatus of claim 2, wherein the control circuit is configured to calculate a plurality of impedance components of the stimulation vector and calculate the capture stimulation threshold of the stimulation vector using the calculated effective impedance of the stimulation vector, the calculated impedance components of the stimulation vector, and the capture current stimulation thresholds.

5. The apparatus of claim 1, wherein the control circuit is configured to generate a recommended minimum pacing stimulation energy for the stimulation vector using the determined capture stimulation threshold of the stimulation vector.

6. The apparatus of claim 1, wherein the first vector electrode is an anode of the stimulation vector and the combined vector electrode is a cathode of the stimulation vector.

7. The apparatus of claim 1, wherein the control circuit is configured to:
   change the stimulation vector to include the first vector electrode and a first single electrode of the combined vector electrode;
   initiate a determination of a minimum stimulation energy level that induces capture of the tissue target as the capture stimulation threshold for the changed stimulation vector;
   change the stimulation vector to include the first vector electrode and a second single electrode of the combined vector electrode and repeat the determination of the minimum stimulation energy level that induces capture; and
   repeat the changing of the single electrode of the combined vector electrode and repeat the iterative stimulation energy delivery until a minimum stimulation energy level that induces capture is determined for a stimulation vector that includes the first vector electrode and each single electrode of the combined vector electrode.

8. The apparatus of claim 7, wherein the capture detection sub-circuit is configured to:
   deliver pacing stimulation energy to the tissue target using a first energy level;
   change the stimulation energy level by at least one of: a) increasing the stimulation energy from the first energy level until detecting that the stimulation energy induces stable capture, or b) reducing the stimulation energy from the first energy level until detecting that the stimulation energy fails to induce capture of the tissue target;
   continue the changing of the stimulation energy level until confirming the stable capture or the failure to induce capture; and
   determine the capture stimulation threshold energy as the stimulation energy level that resulted in stable capture or the last energy stimulation level before failure to induce capture.

9. The apparatus of claim 1, including:
   an impedance measurement circuit electrically coupled to the plurality of implantable electrodes and configured to measure the impedance between any two electrodes included in the stimulation vector,
   wherein the control circuit is configured to calculate an effective impedance of the stimulation vector using impedances measured by the impedance measurement circuit, and calculate longevity of a battery of the implantable medical device using the determined effective impedance and the determined capture stimulation threshold of the stimulation vector.

10. The apparatus of claim 9, including a communication circuit configured to communicate information with a second separate device, including to receive a value for a parameter of the electrical pulse stimulation energy, wherein the control circuit is configured to calculate the longevity of the battery of the ambulatory medical device using the received parameter value, the determined capture stimulation threshold, and the determined effective impedance.

11. A method of controlling operation of an implantable medical device, the method comprising:
configuring a stimulation vector to include a first implantable electrode as a first vector electrode and a plurality of other implantable electrodes electrically coupled together to form a second combined vector electrode;
delivering electrical pacing stimulation to the implantable electrodes included in the stimulation vector;
determining individual stimulation energy level capture thresholds between the first vector electrode and each single electrode of the combined vector electrode; and
determining a stimulation capture threshold of the stimulation vector using the determined individual capture thresholds and generating an indication of the capture threshold.

12. The method of claim 11, including:
calculating an effective impedance of the stimulation vector,
wherein determining individual stimulation energy level capture thresholds includes determining current stimulation capture thresholds between each single electrode of the combined vector electrode and the first vector electrode, and
wherein determining the stimulation capture threshold of the stimulation vector includes calculating the stimulation capture threshold using the calculated effective impedance of the stimulation vector and the current stimulation capture thresholds.

13. The method of claim 12, wherein determining the capture current stimulation thresholds includes:
measuring capture voltage stimulation thresholds between the first vector electrode and each electrode of the combined vector electrode;
measuring impedances between each electrode of the combined vector electrode and the first vector electrode, wherein an impedance is measured while none of the plurality of electrodes are electrically connected together to form the combined vector electrode; and
calculating the capture current stimulation thresholds using the measured impedances and capture voltage stimulation thresholds.

14. The method of claim 12, including calculating a plurality of resistive components of the stimulation vector and wherein determining the capture stimulation threshold of the stimulation vector includes calculating the capture stimulation threshold using the calculated effective impedance of the stimulation vector, the calculated resistive components of the stimulation vector, and the capture current stimulation thresholds.

15. The method of claim 12, wherein determining capture stimulation thresholds between the first vector electrode and each single electrode of the combined vector electrode:
changing the stimulation vector to include the first vector electrode and a first single electrode of the combined vector electrode;
iteratively delivering stimulation energy to a tissue target of the subject while changing a stimulation energy level;
determining a minimum stimulation energy level that induces capture of the tissue target as the capture stimulation threshold;
changing the stimulation vector to include the first vector electrode and a second single electrode of the combined vector electrode and repeating the iterative stimulation energy delivery and the determining of the minimum stimulation energy level that induces capture; and
repeating the changing of the single electrode of the combined vector electrode and repeating the iterative stimulation energy delivery until minimum stimulation energy levels that induce capture are determined for stimulation vectors that includes the first vector electrode and each single electrode of the combined vector electrode.

16. The method of claim 11, wherein configuring the stimulation vector includes electrically coupling the plurality of implantable electrodes to form a combined cathode of the stimulation vector and wherein the first vector electrode is an anode of the stimulation vector.

17. An apparatus for coupling to a plurality of electrodes implantable at a plurality of tissue sites of a heart chamber of a subject, the apparatus comprising:
a stimulus circuit configured to deliver electrical pacing stimulation to the plurality of implantable electrodes;
a switch circuit configured to electrically couple different combinations of the electrodes to the stimulus circuit; and
a control circuit to configure a stimulation vector that includes a first vector electrode and a plurality of other electrodes electrically coupled together to form a second combined vector electrode, wherein the control circuit includes a capture detection sub-circuit configured to iteratively deliver stimulation energy to a tissue target of the subject while changing a stimulation energy level; and determine a minimum stimulation energy level that induces capture of the tissue target by the combined vector electrode, and wherein the control circuit is configured to calculate a capture stimulation energy level threshold for the stimulation vector using the minimum stimulation energy level.

18. The apparatus of claim 17, wherein the capture detection sub-circuit is configured to determine a minimum stimulation energy level that induces capture of the tissue target by only one electrode of the combined vector electrode, and wherein the control circuit is configured to calculate the capture stimulation threshold for the stimulation vector using the minimum stimulation energy level that induces capture of the tissue target by only one electrode of the combined vector electrode.

19. The apparatus of claim 17, including a sensing circuit configured to produce an electrical activation signal representative of activation of the tissue target, wherein the capture detection sub-circuit is configured to detect at least one of induced capture of the tissue target or failure to induce capture of the tissue target by detecting a change in morphology of the electrical activation signal.

20. The apparatus of claim 19, wherein capture detection sub-circuit is configured to iteratively reduce the stimulation energy from a first energy level until detecting that a first single electrode of the combined vector electrode fails to induce capture and to generate an indication to identify the first single electrode of the combined vector electrode.

* * * * *